(12) United States Patent
De Wit et al.

(10) Patent No.: US 11,014,810 B1
(45) Date of Patent: May 25, 2021

(54) CARBON CAPTURE, WASTE UPGRADE, AND CHEMICALS PRODUCTION USING IMPROVED FLEXICOKING

(71) Applicant: ExxonMobil Research and Engineering Company, Annandale, NJ (US)

(72) Inventors: Martin De Wit, Brielle (NL); Mohsen N. Harandi, New Hope, PA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 16/775,610

(22) Filed: Jan. 29, 2020

(51) Int. Cl.
   *C01B 3/12* (2006.01)
   *C07C 29/151* (2006.01)
   *C01B 3/02* (2006.01)
   *C01B 3/50* (2006.01)
   *C01C 1/04* (2006.01)

(52) U.S. Cl.
   CPC ............... *C01B 3/12* (2013.01); *C01B 3/02* (2013.01); *C01B 3/025* (2013.01); *C01B 3/50* (2013.01); *C01C 1/04* (2013.01); *C07C 29/1518* (2013.01); *C01B 2203/0283* (2013.01); *C01B 2203/061* (2013.01); *C01B 2203/062* (2013.01); *C01B 2203/068* (2013.01)

(58) Field of Classification Search
   CPC ......... C07C 29/1518; C07C 1/04; C01B 3/12; C01B 3/50; C01B 3/025; C01B 3/02; C01B 2203/0283; C01B 2203/062; C01B 2203/061; C01B 2203/068
   See application file for complete search history.

(56) References Cited

U.S. PATENT DOCUMENTS

| | | |
|---|---|---|
| 3,661,543 A | 5/1972 | Saxton |
| 3,702,516 A | 11/1972 | Luckenbach |
| 3,759,676 A | 9/1973 | Lahn |
| 3,816,084 A | 6/1974 | Moser et al. |
| 4,213,848 A | 7/1980 | Saxton |
| 4,269,696 A | 5/1981 | Metrailer |
| 5,472,596 A | 12/1995 | Kerby et al. |

*Primary Examiner* — Jafar F Parsa
(74) *Attorney, Agent, or Firm* — Hsin Lin

(57) ABSTRACT

Systems and methods are provided for integrating a fluidized coking operation, a reverse osmosis operation, a coke gasification operation and/or processes for production of compounds from the synthesis gas generated during the coke gasification. Conventional FLEXICOKING™ processes may produce carbon dioxide emissions and low Joule Flexigas, as well as waste water containing metals and poor quality coke containing metals, which may be expensive to process, or may require sending to other facilities for further processing. The systems and methods described herein address these issues in an advantageous and economical manner, with improved carbon capture, waste upgrade and chemicals production, while providing high value ash (e.g., for recovery of metals such as vanadium, nickel, sodium, iron, and mixtures thereof) and upgraded coke streams.

25 Claims, 3 Drawing Sheets

CARBON CAPTURE, WASTE UPGRADE, AND CHEMICALS PRODUCTION USING IMPROVED FLEXICOKING

FIELD

Systems and methods are provided for upgrading a rejected coke stream and/or low quality coke in a fluidized coking process, and integration with production of compounds from synthesis gas.

BACKGROUND

Coking is a carbon rejection process that is commonly used for upgrading of heavy oil feeds and/or feeds that ae challenging to process, such as feeds with a low ratio of hydrogen to carbon. In addition to producing a variety of liquid products, typical coking processes can also generate a substantial amount of coke. Because the coke contains carbon, the coke is potentially a source of additional valuable products in a refinery setting. However, fully realizing this potential remains an ongoing challenge.

Coking processes in modern refinery settings can typically be categorized as delayed coking or fluidized bed coking. Fluidized bed coking is a petroleum refining process in which heavy petroleum feeds, typically the non-distillable residues (resids) from the fractionation of heavy oils are converted to lighter, more useful products by thermal decomposition (coking) at elevated reaction temperatures, typically about 480° C. to 590° C. (about 900° F. to 1100° F.) and in most cases from about 500° C. to 550° C. (about 930° F. to 1020° F.). Heavy oils, which may be processed by the fluid coking process include heavy atmospheric resids, petroleum vacuum distillation bottoms, aromatic extracts, asphalts, and bitumens from tar sands, tar pits and pitch lakes of Canada (Athabasca, Alta.), Trinidad, Southern California (Los Angeles), McKittrick (Bakersfield, Calif.), Carpinteria (Santa Barbara County, Calif.), Lake Bermudez (Venezuela) and similar deposits such as those found in Texas, Peru, Iran, Russia and Poland.

Fluidized coking is carried out in a unit with a large reactor containing hot coke particles that are maintained in the fluidized condition at the required reaction temperature with steam injected at the bottom of the vessel, with the average direction of movement of the coke particles being downwards through the bed. The heavy oil feed is heated to a pumpable temperature, typically in the range of 350° C. to 400° C. (~660° F. to 750° F.), mixed with atomizing steam, and fed through multiple feed nozzles arranged at several successive levels in the reactor. Steam is injected into a stripping section at the bottom of the reactor and passes upwards through the coke particles descending through the dense phase of the fluid bed in the main part of the reactor above the stripping section. Part of the feed liquid coats the coke particles in the fluidized bed and is subsequently cracked into layers of solid coke and lighter products that evolve as gas or vaporized liquid. Reactor pressure is relatively low in order to favor vaporization of the hydrocarbon vapors which pass upwards from dense phase into dilute phase of the fluid bed in the coking zone and into cyclones at the top of the coking zone where most of the entrained solids are separated from the gas phase by centrifugal force in one or more cyclones and returned to the dense fluidized bed by gravity through the cyclone diplegs. The mixture of steam and hydrocarbon vapors from the reactor is subsequently discharged from the cyclone gas outlets into a scrubber section in a plenum located above the coking zone and separated from it by a partition. It is quenched in the scrubber section by contact with liquid descending over sheds. A pumparound loop circulates condensed liquid to an external cooler and back to the top shed row of the scrubber section to provide cooling for the quench and condensation of the heaviest fraction of the liquid product. This heavy fraction is typically recycled to extinction by feeding back to the coking zone in the reactor.

The coke particles formed in the coking zone pass downwards in the reactor and leave the bottom of the reactor vessel through a stripper section where they are exposed to steam in order to remove occluded hydrocarbons. The solid coke from the reactor, consisting mainly of carbon with lesser amounts of hydrogen, sulfur, nitrogen, and traces of vanadium, nickel, iron, and other elements derived from the feed, passes through the stripper and out of the reactor vessel to a burner or heater where it is partly burned in a fluidized bed with air to raise its temperature from 480° C. to 700° C. (~900° F. to 1300° F.) to supply the heat required for the endothermic coking reactions, after which a portion of the hot coke particles is recirculated to the fluidized bed reaction zone to transfer the heat to the reactor and to act as nuclei for the coke formation. The balance is withdrawn as coke product. The net coke yield is only about 65 percent of that produced by delayed coking.

The FLEXICOKING™ process, developed by Exxon Research and Engineering Company, is a variant of the fluid coking process that is operated in a unit including a reactor and a heater, but also including a gasifier for gasifying the coke product by reaction with an air/steam mixture to form a low heating value fuel gas. The FLEXICOKING™ process is a non-catalytic thermal conversion process with a continuous and totally contained fluidized bed integrated coking and gasification technology. In this process, fluid coke produced in the reactor is gasified with process steam and air to produce a higher value fuel gas (FLEXIGAS™). For instance, a stream of coke passes from the heater to the gasifier where all but a small fraction of the coke is gasified to a low-BTU gas (~120 BTU/standard cubic feet) by the addition of steam and air in a fluidized bed in an oxygen-deficient environment to form fuel gas comprising carbon monoxide and hydrogen. In a conventional FLEXICOKING™ configuration, the fuel gas product from the gasifier, containing entrained coke particles, is returned to the heater to provide most of the heat required for thermal cracking in the reactor with the balance of the reactor heat requirement supplied by combustion in the heater. A small amount of net coke (about 1 percent of feed) is withdrawn from the heater to purge the system of metals and ash. The liquid yield and properties are comparable to those from fluid coking. The fuel gas product is withdrawn from the heater following separation in internal cyclones that return coke particles through their diplegs.

The FLEXICOKING™ process is described in patents of Exxon Research and Engineering Company, including, for example, U.S. Pat. No. 3,661,543 (Saxton), U.S. Pat. No. 3,759,676 (Lahn), U.S. Pat. No. 3,816,084 (Moser), U.S. Pat. No. 3,702,516 (Luckenbach), U.S. Pat. No. 4,269,696 (Metrailer). A variant is described in U.S. Pat. No. 4,213,848 (Saxton) in which the heat requirement of the reactor coking zone is satisfied by introducing a stream of light hydrocarbons from the product fractionator into the reactor instead of the stream of hot coke particles from the heater. Another variant is described in U.S. Pat. No. 5,472,596 (Kerby) using a stream of light paraffins injected into the hot coke return line to generate olefins. Early work proposed units with a stacked configuration but later units have migrated to a side-by-side arrangement.

Although the fuel gas from the gasifier can be used for heating, due to the low energy content, burning of the fuel gas for heat can still represent a relatively low value use for the carbon in the fuel gas. Similarly, the flue gas generated from the burner of a fluidized coking process has traditionally been viewed as a low value product. Additionally, the primary product stream derived from fluidized coking (including FLEXICOKING™) typically includes gases that are formed during the coking process. After separation of liquid products formed during coking, the remaining gases represent yet another product that is traditionally viewed as a low value product. Further, conventional FLEXICOKING™ processes produce carbon dioxide emissions and low Joule Flexigas, as well as wastewater containing metals and poor quality coke containing metals, which has typically been sent to other facilities for further processing. What is needed are systems and methods that can allow for generation of still higher economic value products from the various gas products generated during fluidized coking type processes.

SUMMARY OF THE INVENTION

Systems and methods are provided for upgrading a rejected coke stream and/or low quality coke in a fluidized coking process, and integration with production of compounds from synthesis gas.

In various aspects, methods are provided for upgrading a rejected coke stream, comprising: (i) collecting at least one first effluent coke stream from a coking operation, wherein the at least one first effluent coke stream comprises at least one metal; (ii) removing particulate matter from the at least one first effluent coke stream to provide at least one second effluent stream; (iii) subjecting the at least one second effluent stream to a separation process, such as reverse osmosis, to provide a relatively pure water portion and a brine portion, wherein the brine portion comprises at least one metal; (iv) passing the brine portion from (iii) to a gasifier, wherein the gasifier is operated under conditions sufficient to upgrade the brine portion into a gas portion, and an ash portion, and (v) recovering the ash portion from (iv), wherein the ash portion comprises at least one metal.

In certain aspects, the particulate matter from (ii) comprises coke fines, and these coke fines are used as a feed for a fluid-bed gasifier.

In another aspect, the purified water portion from (iii) may be passed to at least one boiler feedwater system.

In another aspect, the gas portion from (iv) is used as a feed in the production of syngas. For example, at least a portion of the syngas may be directed to a reactor to produce at least one product selected from the group consisting of methanol, urea, ammonium, hydrogen, ethanol, dimethylether, and hydrocarbons. In certain preferred embodiments, at least a portion of the syngas is directed to a methanol synthesis reactor.

In one aspect, the gas portion from (iv) is combined with a low Joule Flexigas for further processing in a reactor. In certain aspects, the low Joule Flexigas is produced within an integrated coking system. In this manner, the process efficiently and advantageously reduces waste and increases production of syngas.

In one aspect, the gas portion from (iv) may be passed to at least one other operation. For example, the at least one other operation is selected from one or more gasifiers and boilers.

In another aspect, the gasifier in (iv) is operated at a temperature from about 500° C. to about 700° C., preferably at a temperature from about 500° C. to about 640° C., most preferably at a temperature of about 625° C. In certain embodiments, the gasifier in (iv) is operated under conditions using an enriched oxygen feed. In certain embodiments, the gasifier in (iv) is operated under conditions to minimize or prevent slag formation. In certain embodiments, the gasifer is a low temperature gasifier, e.g., such as a TRIG™ Transport Integrated Gasification gasifier.

In certain embodiments, the ash portion in (v) comprises at least one metal selected from the group consisting of vanadium, nickel, sodium, iron, and mixtures thereof.

In certain embodiments, the method described here can lead to greater than about 95% of the rejected coke stream is converted to syngas and ash. Preferably, all of the rejected coke stream is converted to syngas and ash.

The methods described here for upgrading a rejected coke stream can be integrated into a fluidized coking process, or integrated into a delayed coking process. In other embodiments, the methods can be applied downstream of a residue conversion process that use hydrogen addition. Examples of such residue conversion processes include LC-Fining, H-oil, Slurry Hydrocracking, and Veba Combi Cracking. In yet another aspect, these methods can be applied for processing the pitch from a solvent de-asphalting unit.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
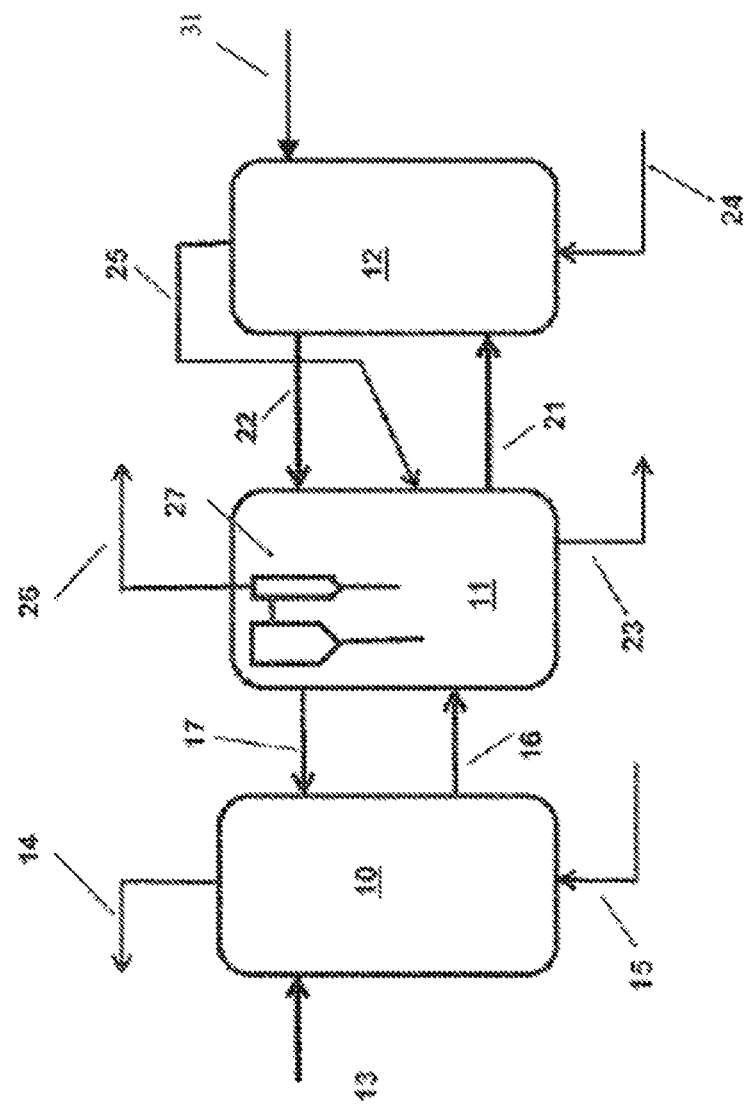
FIG. 1 shows an example of a fluidized bed coking system including a coking reactor, a heater, and a gasifier.

In various aspects, systems and methods are provided for integrating a coking process, e.g., such as a fluidized coking process with a coke gasification process, and processes for production of additional products from the coking and/or gasification process. The integrated processes provide improved carbon capture, waste upgrade and/or chemicals production, preferably while providing high value ash (e.g., for recovery of metals such as vanadium, nickel, sodium, iron, and mixtures thereof) and upgraded coke streams.

Conventional FLEXICOKING™ produces wastewater and low quality coke, both of which contain metals. These waste products may need to be treated, or shipped to other facilities for further processing, which could increase cost and carbon dioxide ($CO_2$) emissions. In addition, handling low Joule Flexigas in refinery operations is costly and undesirable. The methods described herein address these issues in an advantageous and economical manner, which provides for carbon capture, waste upgrade and chemicals production.

The present application relates to a processing scheme, which is suitable for recovering carbon dioxide ($CO_2$) from Low Joules Flexigas, while making a relatively large volume of syngas. The improved yield of syngas helps the economy of scale, where the process can advantageously produce ammonia ($NH_3$), urea, or other chemicals such as hydrogen ($H_2$), methanol, ethanol and/or derivatives thereof. The methods may also provide an increase in the volume of syngas by about 15%, by using a dedicated fluid bed system to burn the rejected coke streams. The fluid-bed system operates at milder gasification conditions, which eliminate or minimize the formation of liquid slag. In certain embodiments, this can provide sufficient scale for a world-scale $NH_3$ plant, integrated in a world-scale FLEXICOKER™, gaining economy of scale. In certain embodiments, the additional syngas can optionally be mixed with the Flexigas for processing in one processing section.

In certain embodiments, one or more waste water streams are first processed to separate high quality water for use in refinery operations (such as boilers) and the fines with water rejects are used as a feed to the dedicated fluid-bed gasifier as steam feed. This allows gasifying the coke particles, while the metal particles will deposit on the high metal content circulating solids. In certain embodiments, the metals in coke are upgraded to valuable ore. This is achieved in a dedicated fluid-bed where the ash recovered will contain valuable metals in a concentrated form. Advantageously, by using the processes described herein, all of the rejected coke streams and waste water will be converted into useful products, i.e., syngas and high value ash, in the dedicated fluid-bed system. As such, it will not be necessary to transport or process coke in other plants, thereby reducing emissions and decreasing production costs.

The thermal cracking of heavy petroleum feeds occurs in processes such as delayed coking, visbreaking, catalytic cracking, FLEXICOKING™ and FLUID COKING™. Preferred thermal cracking processes include FLEXICOKING™ and FLUID COKING™. Heavy petroleum feeds include heavy hydrocarbonaceous oils, heavy and reduced petroleum crude oil, petroleum atmospheric distillation bottoms, petroleum vacuum distillation bottoms, or residuum, pitch, asphalt, bitumen, other heavy hydrocarbon residues, tar sand oil, shale oil, coal, coal slurries, liquid products derived from coal liquefaction processes, including coal liquefaction bottoms, and mixtures thereof.

In delayed coking, heavy feed is sent to a coke drum. The feed is heated to the coking point wherein the heat is supplied in a furnace and the heated feed is then introduced to the coke drum where the residence time for the coking reactions is provided. The coke drums are usually run in parallel so that one drum can be used for coking while the other drum is being cleaned of coke. Delayed coking produces sponge coke, needle coke or shot coke, depending on feed and reactor conditions and the presence of additives in the feed. Delayed cokers do not typically use cyclones as the feed to be coked is heated to the coking temperature and held in the coker drum until a solid mass of coke is formed in the drum. Vapors from the coke drum are sent to a fractionator where they are separated into product cuts based on boiling points. The full drum is steamed to remove remaining hydrocarbons. Coke is removed from the cooled drums by mechanical means such as a drill or by using a hydraulic system usually comprising a multiplicity of high pressure water jets.

Fluidized coking process may also be used. The preferred FLEXICOKING™ or FLUID COKING™ is based on fluidized bed technology developed by ExxonMobil. The fluidized bed coking unit can be any conventional fluidized bed coking process unit and its specific configuration is not critical to the present invention. Both FLEXICOKING™ and FLUID COKING™ use similar coking reactors. FLEXICOKING™ includes a reactor, heater and gasifier, while FLUID COKING™ includes a reactor and burner.

In FLUID COKING™, a heavy feedstock, such as a vacuum residuum, is fed to a coking zone comprised of a fluidized bed of hot solid particles, usually coke particles, sometimes also referred to as seed coke. The feedstock is reacted in the coking zone maintained at temperatures is the range of 850° F. to 1200° F. (454° C. to 649° C.), resulting in conversion products which include a vapor fraction and coke, which coke is deposited on the surface of the seed coke particles. A portion of the coked-seed particles is sent to a heating zone which is maintained at a temperature higher than that of the coking zone. Some of the coke is burned off in the heating zone. Hot seed particles from the heating zone are returned to the coking zone as regenerated seed particles, which serve as the primary heat source for the coking zone. Solid particles are separated from vapor products in a cyclone. Vapor products are then sent to a fractionator.

In this description, the term "FLEXICOKING" (trademark of ExxonMobil Research and Engineering Company) is used to designate a fluid coking process in which heavy petroleum feeds are subjected to thermal cracking in a fluidized bed of heated solid particles to produce hydrocarbons of lower molecular weight and boiling point along with coke as a by-product which is deposited on the solid particles in the fluidized bed. The resulting coke can then converted to a fuel gas by contact at elevated temperature with steam and an oxygen-containing gas in a gasification reactor (gasifier). This type of configuration can more generally be referred to as an integration of fluidized bed coking with gasification.

In a FLEXICOKING™ process, a third major vessel is added to gasify the product coke. A coking reactor, a heater (vs. burner) vessel, and a gasifier are integrated into a common fluidized-solids circulating system. A material stream circulates continuously between a reactor and a heater. More specifically, a feed stream is fed into a fluidized bed, along with a stream of hot recirculating material. From the reactor, a stream containing coke is circulated to a heater vessel, where it is heated. The hot coke stream is sent from the heater to a gasifier, where it reacts with air and steam. The gasifier product gas, referred to as coke gas, containing entrained coke particles, is returned to the heater and cooled by cold coke from the reactor to provide a portion of the reactor heat requirement. A return stream of coke sent from the gasifier to the heater provides the remainder of the heat requirement. Hot coke gas leaving the heater is used to generate high-pressure steam before being processed for cleanup. Coke is continuously removed from the reactor. The purge coke (about 0.5% of the product coke) from the FLEXICOKING™ process normally contains about 99% of the feed metals and has a volatile content of 2 wt. % to 7 wt. %.

A general method that applies to FLEXICOKING™ methods and fluid-bed coking methods includes the following steps: introducing a hydrocarbon feed stream into a coking zone of a reactor containing a fluidized bed of coke particles maintained at coking temperatures (e.g., about 40° C. to about 1050° C., preferably about 150° C. to about 900° C., about 300° C. to about 1050° C., preferably about 300°

C. to about 750° C., and more preferably about 450° C. to about 650° C.) to produce a vapor phase hydrocarbon product while coke is deposited on the coke particles; introducing a steam stream into a stripper section of the reactor; allowing the coke particles to pass downwards in the reactor to a stripper section of the reactor; transferring the coke particles from the stripper section of the reactor to a gasifier/burner; contacting the coke particles in the gasifier/burner an oxygen-containing gas in an oxygen-limited atmosphere at an elevated temperature to heat the coke particles and form a fuel gas product that comprises carbon monoxide and hydrogen; recycling the heated coke particles from the gasifier/burner to the coking zone of the reactor; and introducing at least one waste stream to the reactor and/or the gasifier/burner.

In fluid-bed coking methods, a burner is used. In FLEXICOKING™ methods, a gasifier is used. In some FLEXICOKING™ methods, a heater section (also referred to herein simply as a heater) is included between the reactor and the gasifier.

A cyclone system is typically used to remove coke fines from the fuel gas. For example, a cyclone system can include serially connected primary and secondary cyclones with diplegs that return the separated fines to the fluid bed in the vessel in which the cyclone system is connected or a part of. The cyclone system can be a portion of the gasifier/burner. When a heater section is included in FLEXICOKING™ methods, the cyclone system can be included as part of the heater section.

Typically, the coking zone of the reactor operates at about 450° C. to about 850° C., and the combustion or gasification zone of the burner operate at about 850° C. to about 1000° C. However, depending on the composition of the waste streams, these zones of the reactor and burner or gasifier may be operated at a higher temperature to reduce buildup sticky, adherent high molecular weight hydrocarbon deposits on the particles that could lead to reactor fouling. For higher operating temperatures, the coking zone of the reactor operates at about 850° C. to about 1050° C., and the combustion or gasification zone of the burner or gasifier operate at about 1000° C. to about 1200° C. where the combustion or gasification zone is at a higher temperature than the coking zone. Therefore, the methods described herein can be performed with the coking zone of the reactor operating at about 450° C. to about 1050° C. and the combustion or gasification zone of the burner or gasifier operating at about 850° C. to about 1200° C. where the combustion or gasification zone is at a higher temperature than the coking zone. Preferably, the coking zone of the reactor operates at about 600° C. to about 1050° C. and the combustion or gasification zone of the burner or gasifier operate at about 950° C. to about 1200° C.

These methods advantageously upgrade waste (hydrocarbon-rich waste and/or water-rich waste) to fuel gas and hydrocarbon product. The fuel gas (also known as syngas) is useful as an intermediate when producing, for example, ammonia, methanol, and synthetic hydrocarbon fuels. Further, the hydrocarbon products comprise $C_{5+}$-rich hydrocarbons that can be used in various industrial processes and as components to be processed for blending into gasoline, jet, kerosene, and diesel.

As used here, the term "coke" refers to the solid residue remaining from the pyrolysis of hydrocarbons. The term "coking" refers to a thermal cracking process that converts petroleum residuum, e.g., bottoms from atmospheric and vacuum distillation of crude oil, into upgraded liquid and gas products, leaving behind a solid concentrated carbon material, or "petroleum coke."

The terms "coker" and "coking system" are used interchangeably and refer to an apparatus system used in carrying out the coking process. The term "coking reactor" refers to an apparatus unit of a coking system in which a substantial level of thermal cracking occurs. For example, in a delayed coking process, a coke drum is an example of a coking reactor.

A "carbon rejection" process is a chemical process that results in the production of elemental carbon (such as petroleum coke) and therefore a reduction in carbon content (rejection) in the liquid hydrocarbons involved.

The terms "upgrade", "upgrading" and "upgraded", when used to describe a feedstock that is being or has been subjected to hydroprocessing, or a resulting material or product, shall refer to one or more of a reduction in the molecular weight of the feedstock, a reduction in the boiling point range of the feedstock, a reduction in the concentration of asphaltenes, a reduction in the concentration of hydrocarbon free radicals, and/or a reduction in the quantity of impurities, such as sulfur, nitrogen, oxygen, halides, and metals.

As used herein, the term "resid" refers to the complex mixture of heavy petroleum compounds otherwise known in the art as residuum or residual.

As used herein, the term "fuel gas" refers to a gas comprising carbon monoxide and hydrogen in a combined concentration of at least 20 wt %, preferably at least 30 wt %, and more preferably at least 90 wt %. Carbon dioxide and/or nitrogen may also be included in fuel gas.

Methods and Systems Using Fluidized Coking with Integrated Gasification

In various aspects, an integrated fluidized bed coker and gasifier, optionally also including a heater, can be used to process a feed by first coking the feed and then gasifying the resulting coke. This can generate a fuel gas product (withdrawn from the gasifier or the optional heater) that can then be further processed to increase the concentration of synthesis gas in the product. The product with increased synthesis gas concentration can then be used as an input for production of methanol, optionally after further processing to adjust the $H_2$ to CO ratio in the synthesis gas.

The FLEXICOKING™ unit may be a conventional three-vessel unit of cracking reactor, heater, and gasifier or, alternatively, a two-vessel unit of reactor and gasifier in which the coke from the reactor passes directly to the gasifier and hot, partly gasified coke particles from the gasifier are cycled back to the reactor to provide the heat for the endothermic cracking reactions. A unit of this type is described in U.S. Patent Application Publication No. 2015/0368572 (Rajagopalan), to which reference is made for a description of the unit and its method of operation.

For illustrative purposes only, a fluidized bed coking process unit reactor is shown in the figures. FIG. 1 shows an example of a FLEXICOKER™ unit (i.e., a system including a gasifier that is thermally integrated with a fluidized bed coker) with three reaction vessels: reactor, heater, and gasifier. The unit comprises reactor section 10 with the coking zone and its associated stripping and scrubbing sections (not separately indicated), heater section 11 and gasifier section 12. The relationship of the coking zone, scrubbing zone and stripping zone in the reactor section is shown, for example, in U.S. Pat. No. 5,472,596, to which reference is made for a description of the FLEXICOKING™ unit and its reactor section. A heavy oil feed is introduced into the unit by line 13 and cracked hydrocarbon product withdrawn through line 14. Fluidizing and stripping steam is supplied by line 15. Cold coke is taken out from the stripping section at the base of reactor 10 by means of line 16 and passed to heater 11. The term "cold" as applied to the temperature of the withdrawn coke is, of course, decidedly relative since it is well above ambient at the operating temperature of the stripping section. Hot coke is circulated from heater 11 to reactor 10 through line 17. Coke from heater 11 is transferred to gasifier 12 through line 21 and hot, partly gasified particles of coke are circulated from the gasifier back to the heater through line 22. The excess coke is withdrawn from the heater 11 by way of line 23. In conventional configurations, gasifier 12 is provided with its supply of steam and air by line 24 and hot fuel gas is taken from the gasifier to the heater though line 25. In various aspects, instead of supplying air via a line 24 to the gasifier 12, a stream of oxygen with 55 vol % purity or more can be provided, such as an oxygen stream from an air separation unit. In such aspects, in addition to supplying a stream of oxygen, a stream of an additional diluent gas can be supplied by line 31. The additional diluent gas can correspond to, for example, $CO_2$ separated from the fuel gas generated during the gasification. The fuel gas is taken out from the unit through line 26 on the heater; coke fines are removed from the fuel gas in heater cyclone system 27 comprising serially connected primary and secondary cyclones with diplegs that return the separated fines to the fluid bed in the heater. The fuel gas from line 26 can then undergo further processing for separation of $CO_2$ (and/or $H_2S$) and conversion of synthesis gas to methanol.

It is noted that in some optional aspects, heater cyclone system 27 can be located in a separate vessel (not shown) rather than in heater 11. In such aspects, line 26 can withdraw the fuel gas from the separate vessel, and the line 23 for purging excess coke can correspond to a line transporting coke fines away from the separate vessel. These coke fines and/or other partially gasified coke particles that are vented from the heater (or the gasifier) can have an increased content of metals relative to the feedstock. For example, the weight percentage of metals in the coke particles vented from the system (relative to the weight of the vented particles) can be greater than the weight percent of metals in the feedstock (relative to the weight of the feedstock). In other words, the metals from the feedstock are concentrated in the vented coke particles. Since the gasifier conditions avoid the creation of slag, the vented coke particles correspond to the mechanism for removal of metals from the coker/gasifier environment. In some aspects, the metals can correspond to a combination of nickel, vanadium, and/or iron. Additionally or alternately, the gasifier conditions can cause substantially no deposition of metal oxides on the interior walls of the gasifier, such as deposition of less than 0.1 wt % of the metals present in the feedstock introduced into the coker/gasifier system, or less than 0.01 wt %.

In configurations such as FIG. 1, the system elements shown in the figure can be characterized based on fluid communication between the elements. For example, reactor section 10 is in direct fluid communication with heater 11. Reactor section 10 is also in indirect fluid communication with gasifier 12 via heater 11.

As an alternative, integration of a fluidized bed coker with a gasifier can also be accomplished without the use of an intermediate heater. In such alternative aspects, the cold coke from the reactor can be transferred directly to the gasifier. This transfer, in almost all cases, will be unequivocally direct with one end of the tubular transfer line connected to the coke outlet of the reactor and its other end connected to the coke inlet of the gasifier with no intervening reaction vessel, i.e., heater. The presence of devices other than the heater is not however to be excluded, e.g., inlets for lift gas etc. Similarly, while the hot, partly gasified coke particles from the gasifier are returned directly from the gasifier to the reactor this signifies only that there is to be no intervening heater as in the conventional three-vessel FLEXICOKER™ but that other devices may be present between the gasifier and the reactor, e.g., gas lift inlets and outlets.

Figure 2:
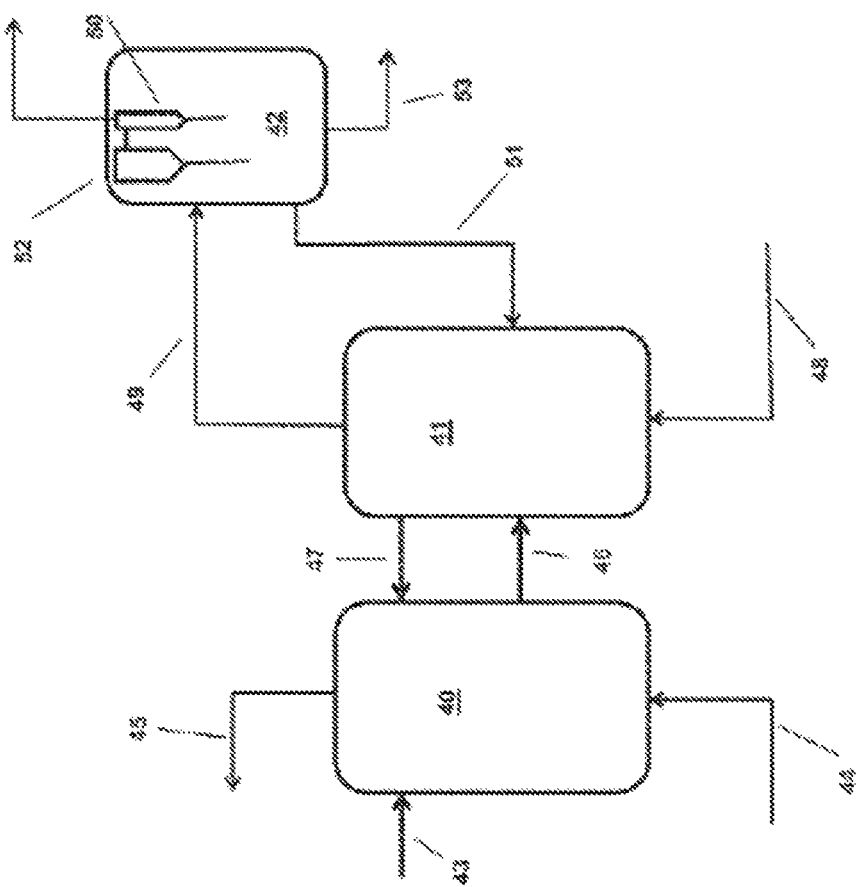
FIG. 2 shows an example of a fluidized bed coking system including a coking reactor and a gasifier.

FIG. 2 shows an example of integration of a fluidized bed coker with a gasifier but without a separate heater vessel. In the configuration shown in FIG. 2, the cyclones for separating fuel gas from catalyst fines are located in a separate vessel. In other aspects, the cyclones can be included in gasifier vessel 41.

In the configuration shown in FIG. 2, the configuration includes a reactor 40, a main gasifier vessel 41 and a separator 42. The heavy oil feed is introduced into reactor 40 through line 43 and fluidizing/stripping gas through line 44; cracked hydrocarbon products are taken out through line 45. Cold, stripped coke is routed directly from reactor 40 to gasifier 41 by way of line 46 and hot coke returned to the reactor in line 47. Steam and oxygen are supplied through line 48. The flow of gas containing coke fines is routed to separator vessel 42 through line 49 which is connected to a gas outlet of the main gasifier vessel 41. The fines are separated from the gas flow in cyclone system 50 comprising serially connected primary and secondary cyclones with diplegs, which return the separated fines to the separator vessel. The separated fines are then returned to the main gasifier vessel through return line 51 and the fuel gas product taken out by way of line 52. Coke is purged from the separator through line 53. The fuel gas from line 52 can then undergo further processing for separation of $CO_2$ (and/or $H_2S$) and conversion of synthesis gas to methanol.

Figure 3:
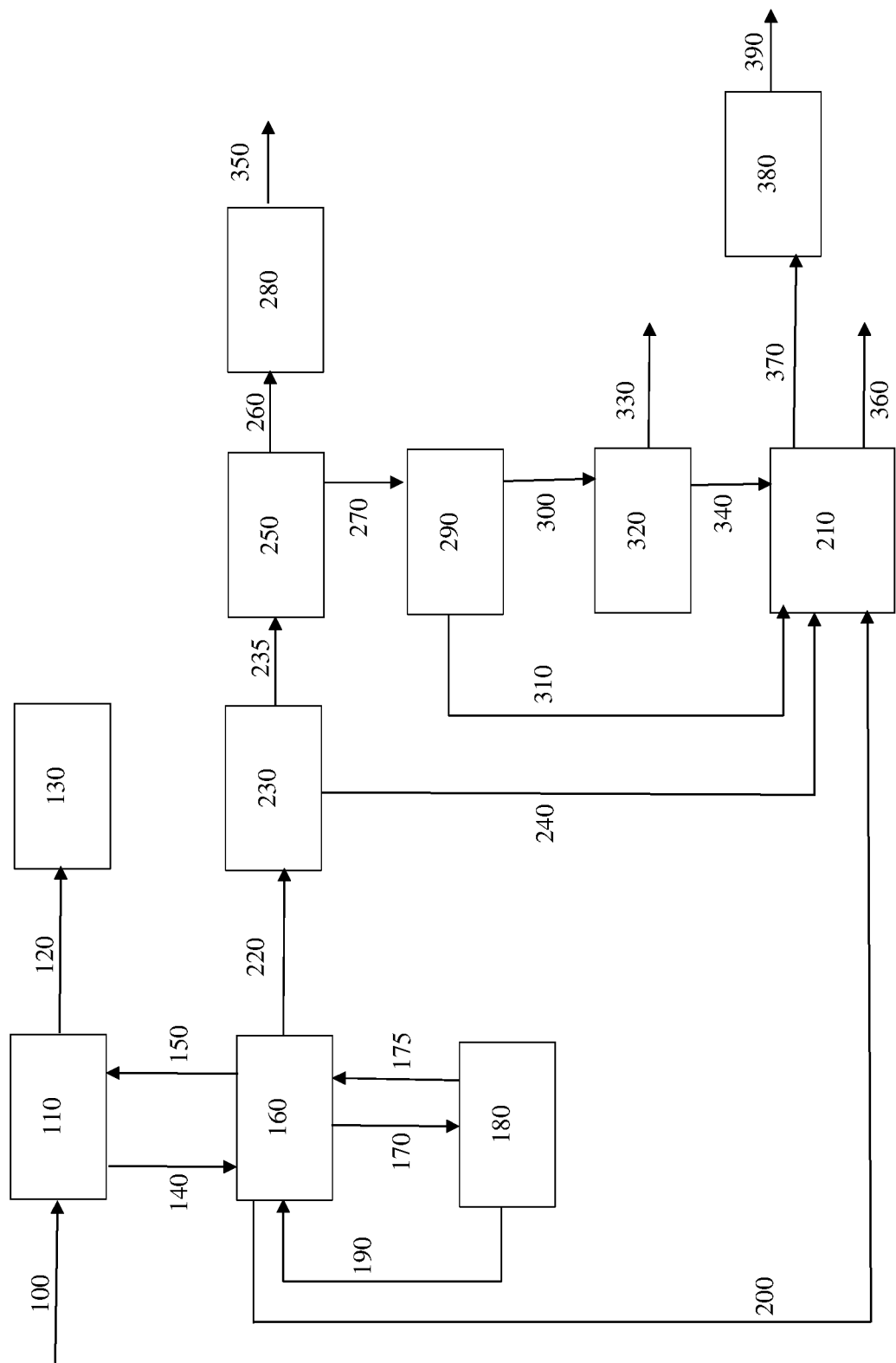
FIG. 3 schematically shows an example of a configuration for integrating fluidized coking with production of methanol, ammonia, and/or other products derived at least in part from a synthesis gas. The integrated process also provides improved carbon capture and waste upgrade, while providing high value ash (e.g., for recovery of metals such as vanadium, nickel, sodium, iron, and mixtures thereof) and upgraded coke streams.

FIG. 3 shows one embodiment of a fluidized bed coker, demonstrating how sour water effluent streams and waste streams are directed to a reverse osmosis operation, followed by gasification, resulting in production of syngas and recovered ash comprising one or more metals (e.g., V, Ni, Na and Fe). As shown in FIG. 3, the residual feed 100 is routed to a FLEXICOKER™ 110, as described above, which produces a full range of cracking products 120 that are subjected to product treating 130. Rejected bed coke 140 from the FLEXICOKER™ operation is passed to a heater 160 and some coke is returned to the FLEXICOKER™ 110 through line 150. After heating, the heated coke 170 is sent to a gasifier 180 (e.g., such as the TRIG gasifier) where it is treated with air and steam. The remaining coke is returned from gasifier 180 to heater 160 through line 175 and raw syngas 190 produced in the gasifier 180 is recycled to the heater 160. Rejected bed coke 200 from heater 160 is sent to gasifier 210 (e.g., such as the TRIG gasifier). Particles 220 are removed from heater 160 and sent to a dry particle removal unit 230, from dry particle removal unit 230 rejected dry fines 240 are sent to gasifier 210. The remaining particles in dry particle removal unit 230 are sent to wet particle removal unit 250 where they are separated into first departiculated raw syngas 260 and coke slurry 270. The first departiculated raw syngas 260 is sent on to desulfurization unit 280 while the coke slurry 270 is sent to particle removal unit 290. Desulfurization unit 280 treats the raw syn gas to create clean syngas 350. Particle removal unit 290 separates coke slurry 270 into sour water 300 and rejected wet fines 310, which are sent to gasifier 210. The sour water 300 is subjected to reverse osmosis 320 where it is separated into demineralized water 330 and brine 340. Brine 340 is sent to gasifier 210. Gasifier 210 treats incoming rejected bed coke 200, rejected dry fines 240, rejected wet fines 310, and brine 340 to create a high metal ash 360 and second departiculated raw syngas 380. Second departiculated raw syngas 370 is sent on to desulfurization unit 380 that treats the second departiculated raw syngas to create clean syngas 390

The coker and gasifier can be operated according to the parameters necessary for the required coking processes. Thus, the heavy oil feed will typically be a heavy (high boiling) reduced petroleum crude; petroleum atmospheric distillation bottoms; petroleum vacuum distillation bottoms, or residuum; pitch; asphalt; bitumen; other heavy hydrocarbon residues; tar sand oil; shale oil; or even a coal slurry or coal liquefaction product such as coal liquefaction bottoms. Such feeds will typically have a Conradson Carbon Residue (ASTM D189-165) of at least 5 wt. %, generally from about 5 to 50 wt. %. Preferably, the feed is a petroleum vacuum residuum.

More generally, the feed to the fluidized bed coker can have a T10 distillation point of 343° C. or more, or 371° C. or more.

The heavy oil feed, pre-heated to a temperature at which it is flowable and pumpable, is introduced into the coking reactor towards the top of the reactor vessel through injection nozzles that are constructed to produce a spray of the feed into the bed of fluidized coke particles in the vessel. Temperatures in the coking zone of the reactor are typically in the range of about 450° C. to about 850° C. and pressures are kept at a relatively low level, typically in the range of about 120 kPag to about 400 kPag (about 17 psig to about 58 psig), and most usually from about 200 kPag to about 350 kPag (about 29 psig to about 51 psig), in order to facilitate fast drying of the coke particles, preventing the formation of sticky, adherent high molecular weight hydrocarbon deposits on the particles which could lead to reactor fouling. The conditions can be selected so that a desired amount of conversion of the feedstock occurs in the fluidized bed reactor. The coking reaction and the amount of conversion can be selected to be similar to the values used in a conventional fluidized coking reaction. For example, the conditions can be selected to achieve at least 10 wt % conversion relative to 343° C. (or 371° C.), or at least 20 wt % conversion relative 343° C. (or 371° C.), or at least 40 wt % conversion relative to 343° C. (or 371° C.), such as up to 80 wt % conversion or possibly still higher. The light hydrocarbon products of the coking (thermal cracking) reactions vaporize, mix with the fluidizing steam and pass upwardly through the dense phase of the fluidized bed into a dilute phase zone above the dense fluidized bed of coke particles. This mixture of vaporized hydrocarbon products formed in the coking reactions flows upwardly through the dilute phase with the steam at superficial velocities of about 1 to 2 meters per second (about 3 to 6 feet per second), entraining some fine solid particles of coke which are separated from the cracking vapors in the reactor cyclones as described above. The cracked hydrocarbon vapors pass out of the cyclones into the scrubbing section of the reactor and then to product fractionation and recovery.

In this discussion, reference may be made to conversion of a feedstock relative to a conversion temperature. Conversion relative to a temperature can be defined based on the portion of the feedstock that boils at greater than the conversion temperature. The amount of conversion during a process (or optionally across multiple processes) can correspond to the weight percentage of the feedstock converted from boiling above the conversion temperature to boiling below the conversion temperature. As an illustrative hypothetical example, consider a feedstock that includes 40 wt % of components that boil at 650° F. (~343° C.) or greater. By definition, the remaining 60 wt % of the feedstock boils at less than 650° F. (~343° C.). For such a feedstock, the amount of conversion relative to a conversion temperature of ~343° C. would be based only on the 40 wt % that initially boils at ~343° C. or greater. If such a feedstock could be exposed to a process with 30% conversion relative to a ~343° C. conversion temperature, the resulting product would include 72 wt % of ~343° C.– components and 28 wt % of ~343° C.+ components.

As the cracking process proceeds in the reactor, the coke particles pass downwardly through the coking zone, through the stripping zone, where occluded hydrocarbons are stripped off by the ascending current of fluidizing gas (steam). They then exit the coking reactor and pass to the gasification reactor (gasifier) which contains a fluidized bed of solid particles and which operates at a temperature higher than that of the reactor coking zone. In the gasifier, the coke particles are converted by reaction at the elevated temperature with steam and an oxygen-containing gas into a fuel gas comprising carbon monoxide and hydrogen.

The gasification zone is typically maintained at a high temperature ranging from about 850° C. to about 1000° C. (about 1560° F. to 1830° F.) and a pressure ranging from about 0 kPag to about 1000 kPag (about 0 psig to about 150 psig), preferably from about 200 kPag to about 400 kPag (about 30 psig to about 60 psig). Steam and an oxygen-containing gas, including air, or a gas stream having a low nitrogen content, such as oxygen from an air separation unit or another oxygen stream including 22 vol % or more of oxygen, 95 vol % or more of oxygen, or 98 vol % or more, are passed into the gasifier for reaction with the solid particles comprising coke deposited on them in the coking zone. A separate diluent stream, such as a recycled $CO_2$ or $H_2S$ stream derived from the fuel gas produced by the gasifier, can also be passed into the gasifier. The amount of diluent can be selected by any convenient method. For example, the amount of diluent can be selected so that the amount of diluent replaces the weight of $N_2$ that would be present in the oxygen-containing stream if air was used as the oxygen-containing stream. As another example, the amount of diluent can be selected to allow for replacement of the same BTU value for heat removal that would be available if $N_2$ was present based on use of air as the oxygen-containing stream. These types of strategy examples can allow essentially the same or a similar temperature profile to be maintained in the gasifier relative to conventional operation.

In the gasification zone the reaction between the coke and the steam and the oxygen-containing gas produces a hydrogen and carbon monoxide-containing fuel gas and a partially gasified residual coke product. Conditions in the gasifier are selected accordingly to generate these products. Steam, oxygen, and $CO_2$ rates will depend upon the rate at which cold coke enters from the reactor and to a lesser extent upon the composition of the coke which, in turn will vary according to the composition of the heavy oil feed and the severity of the cracking conditions in the reactor with these being selected according to the feed and the range of liquid products which is required. The fuel gas product from the gasifier may contain entrained coke solids and these are removed by cyclones or other separation techniques in the gasifier section of the unit; cyclones may be internal cyclones in the main gasifier vessel itself or external in a separate, smaller vessel as described below. The fuel gas product is taken out as overhead from the gasifier cyclones. The resulting partly gasified solids are removed from the gasifier and introduced directly into the coking zone of the coking reactor at a level in the dilute phase above the lower dense phase.

Rejected Coke Stream

In refinery operations, large quantities of water are used for various purposes, particularly purifying fractions, steam distillation, dilution, heat transfer, fluid carrier, etc. The water becomes contaminated with various impurities found in crude petroleum and with other contaminants. This contaminated water, termed sour water, typically contains substantial amounts of undesirable components. With the increase in the size and number of petroleum refineries and the number of processing steps in refining operations, the amount of contaminants in sour water could pollute the environment. Furthermore, it is advantageous to reuse such processing water. Embodiments disclosed herein relate to using sour water or wastewater in order to provide purified water, while at the same time recovering metals and/or carbon capture for the production of various products.

In certain aspects, the embodiments disclosed herein include various methods for upgrading a rejected coke stream that is part of a FLEXICOKING™ operation, e.g., to improve carbon capture, waste upgrade and chemicals production. There are many sources of sour water or wastewater in a refinery, which include but are not limited to distillation, wash systems, fluid catalytic cracking, catalytic reforming, visbreaking, hydrocracking, coking, hydrotreating, etc.

One or more rejected coke streams may be in fluid communication with a gasifier. The methods comprise collecting at least one first effluent coke stream from a coking operation, wherein the at least one first effluent coke stream comprises at least one metal. The first effluent coke stream may be one or more rejected coke streams form a coking operation. The rejected coke stream(s) may be produced at various points during the FLEXICOKING™ process, and more than one coke stream from different parts of the FLEXICOKING™ process may be combined for use in the claimed methods.

The rejected coke streams may contain one or more metals, which could advantageously be collected for use.

The embodiments described herein may include removing particulate matter from the at least one first effluent coke stream to provide at least one second effluent stream. The at least one second effluent stream (without particulate matter) is carried forward, e.g., to a reverse osmosis operation, described below. Meanwhile, particulate matter that was removed from the first effluent coke stream(s) may be used for other operations. For example, in certain aspects, the particulate matter comprises coke fines, and these coke fines are used as a feed in a refinery operation, e.g., used as feed for a fluid-bed gasifier.

The particulate matter may be removed from the at least one first effluent coke stream using any suitable method. For example, particulates may be separated by filtration, scrubbing, as well as by applying gravitational, electrical, and centrifugal techniques.

Reverse Osmosis Operation

The second effluent stream is subjected to a reverse osmosis operation to provide a purified water portion and a brine portion, wherein the brine portion comprises at least one metal. The purified water portion may be used for a refinery operation, e.g., the purified water portion may be passed to at least one boiler feedwater system. Meanwhile, the brine portion may be carried forward to a gasifier, as described below.

Any suitable osmosis operation may be used, such as a reverse osmosis process. Reverse osmosis is a filtration method that removes many types of large molecules and ions from solutions by applying pressure to the solution when it is on one side of a selective membrane. The result is that the solute is retained on the pressurized side of the membrane and the pure solvent is allowed to pass to the other side. To be "selective," this membrane should not allow large molecules or ions through the pores (holes), but should allow smaller components of the solution (such as the solvent) to pass freely.

Gasifier

The brine portion is passed to a gasifier, wherein the gasifier is operated under conditions sufficient to upgrade the brine portion into a gas portion and an ash portion.

In certain aspects, the gasifier may be operated at a temperature from about 500° C. to about 700° C., preferably at a temperature from about 500° C. to about 640° C., more preferably at a temperature of about 625° C. In another aspect, the gasifier may be operated under conditions using an enriched oxygen feed.

Preferably, the gasifier is operated under conditions to minimize or prevent slag formation.

In certain embodiments, the low temperature gasifer is a Kellogg, Brown, & Root (KBR) Transport Gasifier (also known as TRIG™ Transport Integrated Gasification). The TRIG™ Transport Integrated Gasification gasifier is a circulating, fluidized-bed reactor, which operates in either air or oxygen blown modes. The gasifier consists of a mixing zone, riser, disengages, cyclone, standpipe, loopseal, and J-leg. Steam and air/oxygen are mixed together and introduced in the lower mixing zone while fuel, sorbent (for sulfur capture), and additional air or oxygen and steam are added in the upper mixing zone. The steam and air/oxygen, fuel, sorbent, and solids from the standpipe are mixed together in the upper mixing zone. The gas and solids move up the riser before entering the disengager, which separates larger particles by gravity. Most of the solids flow from the disengager into the standpipe, while the remaining solids flow to the cyclone and are removed. The gas then exits the gasifier and enters the primary gas cooler and final particulate cleanup. Collected solids are recycled back to the gasifier mixing zone through the loopseal, standpipe, and J-leg. The solids circulation is maintained with recycled synthesis gas (syngas) or nitrogen as aerating gases. The gasifier operates with an internal temperature range of 580° C. to 650° C., depending on the fuel. The gasifier produces coarse ash extracted from the reactor standpipe. The ash is cooled and discharged from the reactor via a lock hopper. The gasifier operates at a high solids recirculation rate that results in excellent gas-solids contact in a highly turbulent environment, with high heat and mass transfer rates.

Gas Portion

Advantageously, the gas portion from the gasification operation may be passed to at least one other operation, e.g., such as, but not limited to, gasifiers and/or boilers.

In certain embodiments, the gas portion is used as a feed in the production of syngas. For example, at least a portion of the syngas may be directed to a reactor to produce at least one product selected from the group consisting of methanol, urea, ammonium, hydrogen, ethanol, dimethylether, and hydrocarbons. In certain preferred embodiments, at least a portion of the syngas is directed to a methanol synthesis reactor. If $H_2$ gas is produced, it can be prepared essentially pure as a chemical, or if the stream's nitrogen content is not separated, it is possible to use it as low $CO_2$ emission fuel in boilers/cogenerators.

In a preferred ammonia process for upgrading the combined syngas made in the instant invention. The hydrogen and nitrogen rich streams produced in the gasification steps of this invention are upgraded to produce ammonia. Hydrogen is formed and then reacted with nitrogen to produce ammonia in the Haber-Bosch process. Sulfur compounds are removed, e.g., passing through a zinc oxide adsorption bed. After that, the carbon dioxide is removed, e.g., by absorption in an aqueous solvent or amine solution, or by adsorption in pressure swing adsorbers (PSA) using solid adsorption media. Finally, catalytic methanation is used to remove any small residual amounts of carbon monoxide or carbon dioxide from the hydrogen, e.g., $CO+3H_2 \rightarrow CH_4+H_2O$ and $CO_2+4H_2 \rightarrow CH_4+2H_2O$. To produce the ammonia, the hydrogen is catalytically reacted with nitrogen to form anhydrous liquid ammonia, e.g., $3H_2+N_2 \rightarrow 2NH_3$ (also referred to as the Haber-Bosch process).

Preferably $H_2$ is added to the feed to the $NH_3$ plant to fully utilize $N_2$ available in the gasifiers syngas.

In another embodiment, the syngas may be combined with a low Joule Flexigas prior to further processing in a reactor, wherein the low Joule Flexigas is produced within an integrated coking system. In this manner, the process efficiently and advantageously reduces waste and increases production of syngas.

Ash Portion

The ash portion, which comprises at least one metal, may be recovered using any suitable methods known in the art.

In certain preferred embodiments, the ash portion comprises at least one metal selected from the group consisting of vanadium, nickel, sodium, iron, and mixtures thereof.

Coke Conversion

In certain embodiments, the methods method described herein can lead to greater than about 95% of the rejected coke stream is converted to syngas and ash. Preferably, all or substantially all of the rejected coke stream is converted to syngas and ash.

In certain aspects, the methods described herein for upgrading a rejected coke stream can be integrated into a fluidized coking process.

In certain aspects, the methods described herein for upgrading a rejected coke stream can be integrated into a delayed coking process.

In certain aspects, the methods described herein for upgrading a rejected coke stream can be applied downstream of a residue conversion process that use hydrogen addition. Examples of such residue conversion processes include LC-Fining, H-oil, Slurry Hydrocracking, and Veba Combi Cracking. LC-fining is used to efficiently hydrocrack residuum to fuel oils and transportation fuels. These processes produce a "pitch" stream (e.g., unconverted stream with very low H/C ratio and rich in metal contaminants) in between 3 and 30% of fresh feed rate. Another option is processing the "pitch" (de-asphalting unit "rock") from a solvent de-asphalting unit that uses C5 (pentane) as solvent. This pitch can have a CCR (conradson carbon rate, i.e., the amount of coke formed when thermally cracking this material) of 400 to 500 g/kg. Preferably, operating conditions can be varied to achieve a range of conversion and product quality to meet seasonal demands or changes in the crude slate.

For example, the H-Oil process may use ebullated-bed hydrocracking technology to process heavy feedstock residues such as vacuum gasoils (VGO), deasphalted oils (DAO), Coal derived oils, Atmospheric and Vacuum Residue with high metals, CCR, sulfur, nitrogen, asphaltenes and solid contents that can cause rapid catalyst fouling and contamination. The goal is to destruct residue and maximize the production of middle-distillates.

Slurry hydrocracking is a slurried catalytic process used to crack residue feeds to gas oils and fuels. Slurry hydrocracking can be used for upgrading heavy hydrocarbon feedstocks obtained from the distillation of crude oil, including hydrocarbon residues or gas oils from atmospheric column or vacuum column distillation. In slurry hydrocracking, these liquid feedstocks can be mixed with hydrogen and solid catalyst particles, e.g., as a particulate metallic compound such as a metal sulfide, to provide a slurry phase. Slurry hydrocracked effluent may exit the slurry hydrocracking reactor at very high temperatures around 400 to 500° C. (752 to 932° F.). Representative slurry hydrocracking processes are described, for example, in U.S. Pat. Nos. 5,755,955 and 5,474,977.

Veba Combi-Cracker (VCC™) technology is a slurry phase hydrocracking/hydrogenation process for converting petroleum residues at very high conversion rates and liquid yields into high quality distillates or synthetic crude oil in refining, Upstream field upgrading and Coal-to-liquids (CTL) markets. VCC adopts a simple flow sheet architecture with traditional refinery grade equipment.

In certain aspects, the methods described herein for upgrading a rejected coke stream can be applied for processing the pitch from a solvent de-asphalting unit. Solvent deasphalting (SDA) is a separation process in which residues are selectively separated by molecular type by mixing with paraffinic solvents and precipitating out of solution asphaltenes and other residue heavy components. SDA produces a low-contaminant, relatively high hydrogen deasphalted oil product (DAO) and a pitch product that contains the majority of the residue's contaminants (metals, asphaltenes, CCR). The pitch product is typically used for delayed coking feedstock, as a fuel oil blending component, gasifier feed (E-Gas™ gasification technology), or in some cases can be blended into asphalts.

Embodiments disclosed herein include various methods for upgrading a rejected coke stream, comprising: (i) collecting at least one first effluent coke stream from a coking operation, wherein the at least one first effluent coke stream comprises at least one metal; (ii) removing particulate matter from the at least one first effluent coke stream to provide at least one second effluent stream; (iii) subjecting the at least one second effluent stream to a reverse osmosis operation to provide a purified water portion and a brine portion, wherein the brine portion comprises at least one metal; (iv) passing the brine portion from (iii) to a gasifier, wherein the gasifier is operated under conditions sufficient to upgrade the brine portion into a gas portion, and an ash portion, and (v) recovering the ash portion from (iv), wherein the ash portion comprises at least one metal.

In certain embodiments, the low temperature gasifer is a TRIG™ Transport Integrated Gasification gasifier.

In another embodiment, a system for upgrading a rejected coke stream is provided, comprising: (i) a fluidized bed coker comprising at least one outlet for a rejected effluent coke stream; (ii) a membrane unit for a reverse osmosis operation, in fluid communication with the at least one outlet for a rejected effluent coke stream, and wherein the membrane unit is capable of providing a purified water portion and a brine portion, wherein the brine portion comprises at least one metal; (iii) a gasifer in fluid communication with the membrane unit, wherein the gasifier is operated at a temperature from about 500° C. to about 640° C., and wherein the conditions are sufficient to upgrade the brine portion into a gas portion and an ash portion; (iv) a synthesis reactor in fluid communication with the gasifier; (v) a line for passing the brine portion from (ii) to a gasifer inlet; (vi) a line for passing the gas portion from (iii) to another operation; and a line for recovering the ash portion from (iii).

In another embodiment, a method is provided for upgrading a rejected coke stream, comprising: (i) collecting at least one effluent coke stream from a coking operation; (ii) subjecting the effluent stream to a reverse osmosis operation to provide a purified water portion and a brine portion; and (iii) passing the brine portion from (ii) to a gasifier, wherein the gasifier is operated under conditions sufficient to upgrade the brine portion into a gas portion, and an ash portion, wherein the gas portion is used as a feed in the production of syngas. Optionally, the gas portion may be combined with at least one low Joule Flexigas prior to further processing to provide a combined gas. Also, the combined gas is processed with steam in a shift reactor to convert a carbon monoxide (CO) portion into a product comprising carbon dioxide ($CO_2$) and hydrogen ($H_2$), and optionally, recovering the $CO_2$ from the product. In certain aspects, at least a portion of the product is directed to a reactor system to produce at least one product selected from the group consisting of methanol, ethanol, dimethylether, urea, ammonium, hydrogen, and hydrocarbons. In certain aspects, the method may further comprise the step of separating hydrogen from the product and/or combined gas, to provide a hydrogen gas product. In yet another aspect, the method may further comprise the step of separating hydrogen and nitrogen from the product and/or combined gas, to provide a clean-burning fuel consisting essentially of hydrogen and nitrogen.

Each of embodiments above may further have one or more of the following additional elements in any combination:

Element 1: the particulate matter from (ii) comprises coke fines, and these coke fines are used as a feed for a fluid-bed gasifier.

Element 2: the purified water portion from (iii) may be passed to at least one boiler feedwater system.

Element 3: the gas portion from (iv) is used as a feed in the production of syngas. For example, at least a portion of the syngas may be directed to a reactor to produce at least one product selected from the group consisting of methanol, urea, ammonium, hydrogen, ethanol, dimethylether, and hydrocarbons. In certain preferred embodiments, at least a portion of the syngas is directed to a methanol synthesis reactor.

Element 4: the syngas is combined with a low Joule Flexigas prior to further processing in a reactor, wherein the low Joule Flexigas is produced within an integrated coking system. In this manner, the process efficiently and advantageously reduces waste and increases production of syngas.

Element 5: the gas portion from (iv) may be passed to at least one other operation. For example, the at least one other operation is selected from one or more gasifiers and boilers.

Element 6: the gasifier in (iv) is operated at a temperature from about 500° C. to about 640° C., preferably at a temperature of about 625° C. Element 7: the gasifier in (iv) is operated under conditions using an enriched oxygen feed.

Element 8: the gasifier in (iv) is operated under conditions to minimize or prevent slag formation.

Element 9: the ash portion in (v) comprises at least one metal selected from the group consisting of vanadium, nickel, sodium, iron, and mixtures thereof.

Element 10: wherein the method described here can lead to greater than about 95% of the rejected coke stream is converted to syngas and ash. Preferably, all or substantially all of the rejected coke stream is converted to syngas and ash.

Element 11: where the methods described herein for upgrading a rejected coke stream can be integrated into a fluidized coking process.

Element 12: where the methods described herein for upgrading a rejected coke stream can be integrated into a delayed coking process.

Element 13: where the methods described herein for upgrading a rejected coke stream can be applied downstream of a residue conversion process that use hydrogen addition. Examples of such residue conversion processes include LC-Fining, H-oil, Slurry Hydrocracking, and Veba Combi Cracking.

Element 14: where the methods described herein for upgrading a rejected coke stream can be applied for processing the pitch from a solvent de-asphalting unit.

By way of non-limiting example, exemplary combinations applicable to the embodiments described in this application may include any combination with one or more of Elements 1-14, described above.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values.

Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

The invention claimed is:

1. A method for upgrading a rejected coke stream, comprising:
   (i) collecting at least one first effluent coke stream from a coking operation, wherein the at least one first effluent coke stream comprises at least one metal;
   (ii) removing particulate matter from the at least one first effluent coke stream to provide at least one second effluent stream;
   (iii) subjecting the at least one second effluent stream to a reverse osmosis operation to provide a purified water portion and a brine portion, wherein the brine portion comprises at least one metal;
   (iv) passing the brine portion from (iii) to a gasifier, wherein the gasifier is operated under conditions sufficient to upgrade the brine portion into a gas portion, and an ash portion, and
   (v) recovering the ash portion from (iv), wherein the ash portion comprises at least one metal.

2. A method of claim 1, wherein the particulate matter from (ii) comprises coke fines, and wherein the coke fines are used as a feed for a fluid-bed gasifier.

3. A method of claim 1, further comprising passing the purified water portion from (iii) to at least one boiler feedwater system.

4. A method of claim 1, wherein the gas portion from (iv) is used as a feed in the production of syngas.

5. A method of claim 4, wherein the gas portion is combined with at least one low Joule Flexigas prior to further processing in a reactor, and wherein the at least one low Joule Flexigas is produced within an integrated coking system.

6. A method of claim 4, wherein at least a portion of the syngas is directed to a reactor to produce at least one product selected from the group consisting of methanol, urea, ammonium, hydrogen, ethanol, dimethylether, and hydrocarbons.

7. A method of claim 6, wherein at least a portion of the syngas is directed to a methanol synthesis reactor.

8. A method of claim 1, further comprising passing the gas portion from (iv) to at least one other operation.

9. A method of claim 8, wherein the at least one other operation is selected from one or more gasifiers and boilers.

10. A method of claim 1, wherein the gasifier in (iv) is operated at a temperature from about 500° C. to about 640° C.

11. A method of claim 10, wherein the gasifier in (iv) is operated at a temperature of about 625° C.

12. A method of claim 1, wherein the gasifier in (iv) is operated under conditions using an enriched oxygen feed.

13. A method of claim 1, wherein the gasifier in (iv) is operated under conditions to minimize or prevent slag formation.

14. A method of claim 1, wherein the ash portion in (v) comprises at least one metal selected from the group consisting of vanadium, nickel, sodium, iron, and mixtures thereof.

15. A method of claim 1, wherein greater than about 95% of the rejected coke stream is converted to syngas and ash.

16. A method of claim 1, wherein the method is integrated into a fluidized coking process.

17. A method of claim 1, wherein the method is integrated into a delayed coking process.

18. A method of claim 1, wherein the method is applied downstream of a residue conversion process that use hydrogen addition.

19. A method of claim 18, wherein the residue conversion process is selected from the group consisting of LC-Fining, H-oil, Slurry Hydrocracking, and Veba Combi Cracking.

20. A method of claim 1, wherein the method is applied for processing the pitch from a solvent de-asphalting unit.

21. A method for upgrading a rejected coke stream, comprising:
   (i) collecting at least one effluent coke stream from a coking operation;
   (ii) subjecting the effluent stream to a reverse osmosis operation to provide a purified water portion and a brine portion; and
   (iii) passing the brine portion from (ii) to a gasifier, wherein the gasifier is operated under conditions sufficient to upgrade the brine portion into a gas portion, and an ash portion, wherein the gas portion is used as a feed in the production of syngas.

22. A method of claim 21, wherein the gas portion is combined with at least one low Joule Flexigas prior to further processing to provide a combined gas.

23. A method of claim 22, wherein the combined gas is processed with steam in a shift reactor to convert a carbon monoxide (CO) portion into a product comprising carbon dioxide ($CO_2$) and hydrogen ($H_2$), and optionally, recovering the $CO_2$ from the product.

24. A method of claim 23, wherein at least a portion of the product is directed to a reactor system to produce at least one product selected from the group consisting of methanol, ethanol, dimethylether, urea, ammonium, hydrogen, and hydrocarbons.

25. A method of claim 23, further comprising the step of separating hydrogen and nitrogen from the product, to provide a clean-burning fuel consisting essentially of hydrogen and nitrogen.

* * * * *